United States Patent
Taylor et al.

(12)

(10) Patent No.: US 6,258,075 B1
(45) Date of Patent: Jul. 10, 2001

(54) TAMPON WITH ENHANCED LEAKAGE PROTECTION

(75) Inventors: Fiona M. Taylor; Thomas W. Osborn, III; Karen A. Kreutz, all of Cincinnati; George A. M. Butterworth, Loveland, all of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/309,467

(22) Filed: May 10, 1999

Related U.S. Application Data (63) Continuation-in-part of application No. 09/287,994, filed on Apr. 8, 1999, now Pat. No. 6,206,867.

(51) Int. Cl.[7] .................................................. A61F 13/15
(52) U.S. Cl. ..................................... 604/385.18; 604/904
(58) Field of Search ............................. 604/904, 385.17, 604/385.18

(56) References Cited

U.S. PATENT DOCUMENTS

| | | |
|---|---|---|
| 1,731,665 | 10/1929 | Huebsch . |
| 2,123,750 | 7/1938 | Schulz . |
| 2,412,391 | 12/1946 | Crockford . |
| 2,464,310 | 3/1949 | Harwood . |
| 2,566,190 | 8/1951 | Greiner et al. . |
| 3,013,558 | 12/1961 | Leupold . |
| 3,037,506 * | 6/1962 | Penksa ................... 604/904 |
| 3,058,469 | 10/1962 | Crockford . |
| 3,101,714 * | 8/1963 | Penksa ................... 604/904 |
| 3,135,262 | 6/1964 | Kobler et al. . |
| 3,420,234 | 1/1969 | Phelps . |
| 3,572,341 * | 3/1971 | Glassman ................. 604/904 |
| 3,674,029 | 7/1972 | Bates et al. . |
| 3,732,866 | 5/1973 | Accavallo . |
| 3,854,481 * | 12/1974 | Messing ................... 604/904 |
| 3,905,372 | 9/1975 | Denkinger . |
| 3,948,257 | 4/1976 | Bossak . |
| 3,965,905 | 6/1976 | Schoenholz et al. . |
| 3,995,636 * | 12/1976 | Murray et al. ............ 604/904 |
| 4,077,408 * | 3/1978 | Murray et al. ............ 604/904 |
| 4,217,900 * | 8/1980 | Wiegner et al. .......... 604/904 |
| 5,047,024 * | 9/1991 | Glassman ............. 604/385.17 |
| 5,112,348 * | 5/1992 | Glassman ............. 604/385.17 |
| 5,718,675 | 2/1998 | Leijd . |
| 5,800,338 * | 9/1998 | Kollerup et al. ......... 604/904 |

FOREIGN PATENT DOCUMENTS

| | | |
|---|---|---|
| 296 15 883 U 1 | 4/1997 | (DE) . |
| 871689 | 6/1961 | (GB) . |

* cited by examiner

*Primary Examiner*—Dennis Ruhl
(74) *Attorney, Agent, or Firm*—Matthew P. Fitzpatrick; Kevin C. Johnson; Steven W. Miller (57) ABSTRACT

This invention relates to absorbent tampons. More particularly, the invention relates to an improved absorbent tampon having improved leakage performance. Tampons, having a primary absorbent member which is constructed from an absorbent material compressed to a self-sustaining form and a mass of secondary absorbent material are disclosed. The mass of secondary absorbent material is preferably located generally proximate the withdrawal end of the primary absorbent member, and is preferably substantially non-compress, and preferably of a smaller diameter than the primary absorbent member. The mass of secondary absorbent material may be a multiple pieces or one piece. The secondary absorbent material may be attached to the primary absorbent member, the withdrawal cord, or both, or may be integral with one or both of these members. The withdrawal cord of the tampon may have absorbent and non-absorbent zones, especially when the mass of secondary absorbent material is attached to the withdrawal cord. The mass of secondary absorbent material preferably has a lower total absorbency than the primary absorbent member. Preferably, the mass of secondary absorbent material is provided with a driving force to direct fluid toward the primary absorbent member. A preferred method of making a tampon of the present invention is also disclosed.

9 Claims, 4 Drawing Sheets

TAMPON WITH ENHANCED LEAKAGE PROTECTION

CROSS REFERENCE TO RELATED APPLICATIONS

This is a continuation in part of Ser. No. 09/287,994 filed on Apr. 8, 1999, now U.S. Pat. No. 6,206,867.

FIELD OF THE INVENTION

This invention relates to absorbent tampons. More particularly, the invention relates to an improved absorbent tampon having increased leakage protection. This is accomplished with a tampon comprising a primary absorbent member and a mass of secondary absorbent material disposed proximate the withdrawal end of the primary absorbent member.

BACKGROUND OF THE INVENTION

A wide variety of absorbent catamenial tampons have long been known in the art. Most currently commercially available tampons are made from a tampon pledget which has been compressed into a substantially cylindrical form. Tampon pledgets of a variety of types and constructions have been described in the art. Prior to compression, the pledget may be rolled, spirally wound, folded, or assembled as a rectangular pad of absorbent material. Tampons made from a generally rectangular pledget of absorbent material have been popular and successful in the market.

The absorbent catamenial tampons now in use typically comprise absorbent members which are compressed to a generally cylindrical form about three-eighths to one-half inch (about 1.0 cm to 1.3 cm) in diameter and from about 2 cm to 7 cm in length. In order to provide the desired total absorbency, these absorbent members are usually formed from batts larger in size than the vaginal orifice, which are then compressed to the size (with a corresponding increase in rigidity) indicated above in order to facilitate insertion. As fluid is absorbed, these compressed tampons are expected to re-expand toward their original pre-compressed size, and to eventually become large enough to effectively cover the vaginal cavity against fluid leakage or bypass. While it has been found that these compressed tampons perform their intended function tolerably well, even the best of them do not always re-expand sufficiently, or fast enough, to provide good coverage against leakage.

The prior art has long recognized various mechanisms by which tampons might fail to deliver superior performance. One such mechanism is often referred to in the art as "bypass" failure. Bypass failure occurs when the menses travels along the length of the vagina without contacting the tampon, i.e. the tampon fails to intercept the flowing menses.

A variety of approaches have been attempted in the prior art to address bypass and other forms of tampon failure. One series of attempts has included the use of a conventional cylindrical, compressed tampon in combination with a secondary or "backup" structure. One example of such an attempt is described in U.S. Pat. No. 3,101,714 issued to Penska. The Penska device consists of a typical elongated cylindrical body of absorbent material with an absorbent withdrawal cord. A plug or pad of absorbent material is slidably mounted on the cord. During normal flow times, the plug member may be removed from the cord. In times of heavier flow, the plug may be slid upward on the cord, after insertion, to be held in place by the sphincter muscles of the vagina. While appearing to address some of the problems associated with bypass flow, the Penska, device suffers from some significant drawbacks. For example, the withdrawal cord of the device is absorbent which has the tendency to retain deposited fluid along the entire length of the cord and, consequently, outward of the orifice of the vagina. Additionally, the slidable plug of the absorbent device resides at least partially externally to the vagina and is held in place by the sphincter muscles thereof. Because the plug of the Penska device cannot be slid into place until after insertion of the tampon portion, a completely internal disposition (i.e. intervaginal placement) of the plug cannot be achieved.

Another prior art approach is described in U.S. Pat. No. 2,123,750 issued to Schulz. The Schulz device consists of an essentially conventional cylindrically shaped absorbent portion with a withdrawal end "flare" of material attached thereto. The withdrawal end flare, however, is comprised of a non-absorbent material and extends outwardly in the radial direction beyond the outer diameter of the cylindrical absorbent portion. This reduces both the comfort associated with the Schulz device, as well as its effectiveness, since the additional material is non-absorbent and, therefore, of marginal usefulness.

Yet another approach is described in U.S. Pat. No. 3,307,506 also issued to Penska. This device generally consists of a tampon attached by the withdrawal cord thereof to a sanitary napkin. This device also suffers from the disadvantage that only external placement of the secondary absorbent member is possible.

While many of the above-described devices and other tampons currently available have been successful and have gained acceptance in the marketplace, the search for an improved absorbent tampon has continued. Each of the above-described devices suffers from certain drawbacks, as noted, which are addressed by the development of the present invention.

During development of the present invention, it has been found that it is desirable to provide a catamenial tampon which may be constructed of materials such as rayon and cotton which have long been used in the art for absorption of menstrual and other vaginal discharges. Such materials are accepted as safe and effective for such in-vivo application, are readily available, and are sufficiently inexpensive for disposable product application. It is also desirable to design a tampon which may be inserted digitally or through the use of conventional "tube and plunger" applicators since such applicators are well accepted by consumers and are easy and inexpensive to manufacture. It is also desired to provide a tampon which is comfortable and which does not depart from currently approved regulatory absorbency ranges. A superior design will achieve all of these goals, while also minimizing bypass leakage associated with the tampon. This is accomplished through the unique design of the present invention which resides in an optimal location within the vaginal vault and which is provided with a superior mechanism for bypass prevention.

SUMMARY OF THE INVENTION

This invention relates to catamenial tampons, and more particularly, to improved tampons having a primary absorbent member which is constructed from an absorbent material compressed to a self-sustaining form. The primary absorbent member of the tampon has an insertion end and a withdrawal end.

In one embodiment, the tampon preferably includes a withdrawal mechanism attached to the primary absorbent member which extends beyond at least the withdrawal end for removal of the tampon. The tampon also preferably includes in such an embodiment a mass of secondary absorbent material fixedly attached to the withdrawal cord proximate the withdrawal end of the primary absorbent member. The absorbency of the primary absorbent member in this execution is preferably greater than the absorbency of the secondary absorbent member. Additionally, the mass of secondary absorbent material is preferably more hydrophilic than the withdrawal mechanism at least along the location of attachment of the mass of secondary absorbent material to the withdrawal mechanism.

In another embodiment, the tampon preferably includes an embodiment a mass of secondary absorbent material proximate the withdrawal end of the primary absorbent material. The density of the secondary absorbent material is preferably lower than the density of the primary absorbent member. The primary absorbent member and the secondary material are preferably configured such that the primary absorbent member and the secondary absorbent material reside entirely within the vaginal space of the user during wear without extending outwardly therefrom. In this second embodiment, the secondary absorbent material may be joined to a withdrawal mechanism or to the primary absorbent member.

In an additional embodiment, the tampon preferably includes a mass of secondary absorbent material proximate the withdrawal end the primary absorbent member, wherein the diameter of the primary absorbent member is larger than the diameter of the mass of secondary absorbent material. In this third embodiment, the secondary absorbent material is preferably joined to a withdrawal mechanism or to the primary absorbent member. Preferably, the primary absorbent member and the secondary absorbent material are configured such that the primary absorbent member and the secondary material reside entirely within the vaginal space of the wearer without extending outwardly therefrom.

In any of the above-described embodiments, the secondary absorbent material may preferably be substantially non-compressed. The secondary absorbent material may be substantially axially centered about the withdrawal mechanism. The tampon may be provided with a gap between the withdrawal end of the primary absorbent member and the start of the secondary absorbent material. Preferably, the diameter of the primary absorbent core of the tampon is greater than the diameter of the secondary absorbent material. The secondary absorbent material may be provided in a plurality of discrete pieces of absorbent material. The primary absorbent member may optionally comprise a layer structure prior to being compressed to a self-sustaining form. The primary absorbent member may also optionally comprise a chevron shaped pad prior to being compressed to a substantially cylindrical self sustaining form.

One preferred method of making the tampon may include the steps of: providing a continuous strip of absorbent material and cutting this strip into a plurality of individual absorbent pads. The first end of each of these pads has a notch and the second end of each of these pads has a tab of absorbent material, the tab being integral with the pad. A step of attaching a withdrawal cord to at least a portion of each of the pads is also included. The method also includes a step of compressing each pad in at least a radial direction to form a tampon having a primary absorbent member and a mass of secondary absorbent material. The tab portion of the pad results in the mass of secondary absorbent material and the mass of secondary absorbent material remains less compressed than the primary absorbent member.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which:

DETAILED DESCRIPTION OF THE INVENTION

This present invention is directed to an improved absorbent tampon having increased leakage protection. It has been found during development of the present invention that there are several potential mechanisms beyond simple bypass flow which may contribute to tampon leakage. Without wishing to be bound by theory, some of these mechanisms may be explained by the following observations. It has been found that many current tampons show stains on the withdrawal cord associated with incidents of tampon leakage. Therefore, the withdrawal cord of many current tampons may be offering an "escape" route for menses present at the base of the vagina.

During a tampon change, some residual menses may be left near the introitus of the vagina. This may be fluid which was previously absorbed, but which subsequently "squeezed out" of the tampon as it was withdrawn through the sphincter of the vagina. Such residual fluid, particularly if located near the introitus (i.e. in the lower vaginal vault) may not be effectively absorbed by the replacement tampon. This is particularly true of many current tampons which are typically inserted somewhat more deeply within the vaginal canal. These mechanisms, as well as bypass described above, and other leakage mechanisms are addressed by the development of the present invention.

Figure 1:
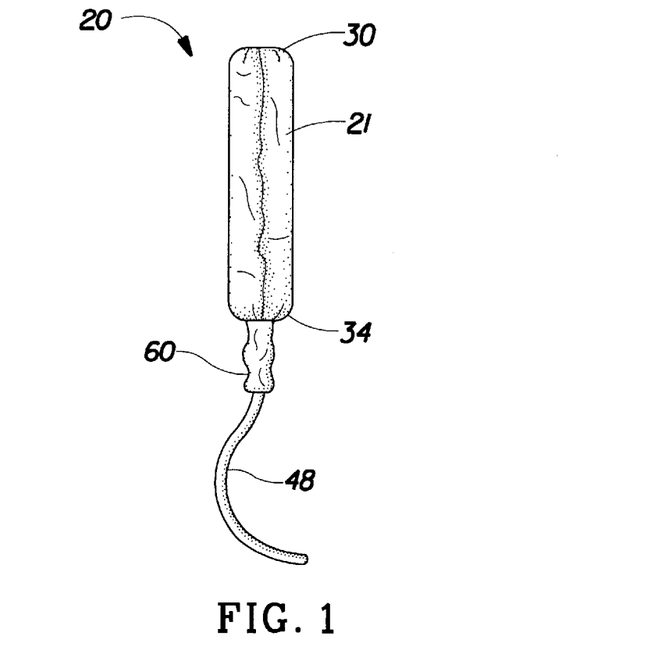
FIG. 1 is a front view of a tampon of the present invention incorporating a primary absorbent member and a mass of secondary absorbent material.

FIG. 1 shows one embodiment of such an absorbent tampon, tampon 20. The present invention, however, is not limited to a structure having the particular configuration shown in the drawings.

As used herein the term "tampon" refers to any type of absorbent structure which is inserted into the vaginal canal or other body cavities for the absorption of fluid therefrom. Typically, tampons are constructed from an absorbent material which has been compressed in either the radial direction, the axial direction, or both in order to provide a tampon which is of a size and stability to allow insertion within the vagina or other body cavity. A tampon which has been so compressed is referred to herein as a "self-sustaining" form. That is, the degree of compression applied to the absorbent material of the tampon pledget is sufficient so that in the subsequent absence of the external forces, the resulting tampon will tend to retain its general shape and size.

It will be understood by one of skill in the art that this self-sustaining form need not, and preferably does not persist during actual use of the tampon. That is once the tampon is inserted and begins to acquire fluid, the tampon will begin to expand and may lose its self-sustaining form.

As used herein the terms "pledget" or "tampon pledget" are intended to be interchangeable and refer to a construction of absorbent material prior to the compression of such construction into a tampon as described above. Tampon pledgets are sometimes referred to as a tampon blank, or a softwind, and the term "pledget" is intended to include such terms as well.

As used herein the terms "vaginal cavity," "within the vagina" and "vaginal interior," are intended to be synonymous and refer to the internal genitalia of the human female in the pudendal region of the body. The term "vaginal cavity" as used herein is intended to refer to the space located between the introitus of the vagina (sometimes referred to as the sphincter of the vagina) and the cervix and is not intended to include the interlabial space, including the floor of vestibule. The externally visible genitalia generally is not included within the term "vaginal cavity" as used herein.

The primary absorbent member 21 (sometimes also referred to as the "absorbent core") of the tampon 20 shown in FIG. 1 has an insertion end 30 and a withdrawal end 34. The primary absorbent member 21 may be compressed into a generally cylindrical configuration in the radial direction, the axial direction, or in both the radial and axial directions. While the primary absorbent member 21 is preferably compressed into a substantially cylindrical configuration, other shapes are also possible. These may include shapes having a cross section which may be described as rectangular, triangular, trapezoidal, semi-circular, or other suitable shapes.

Figure 2:
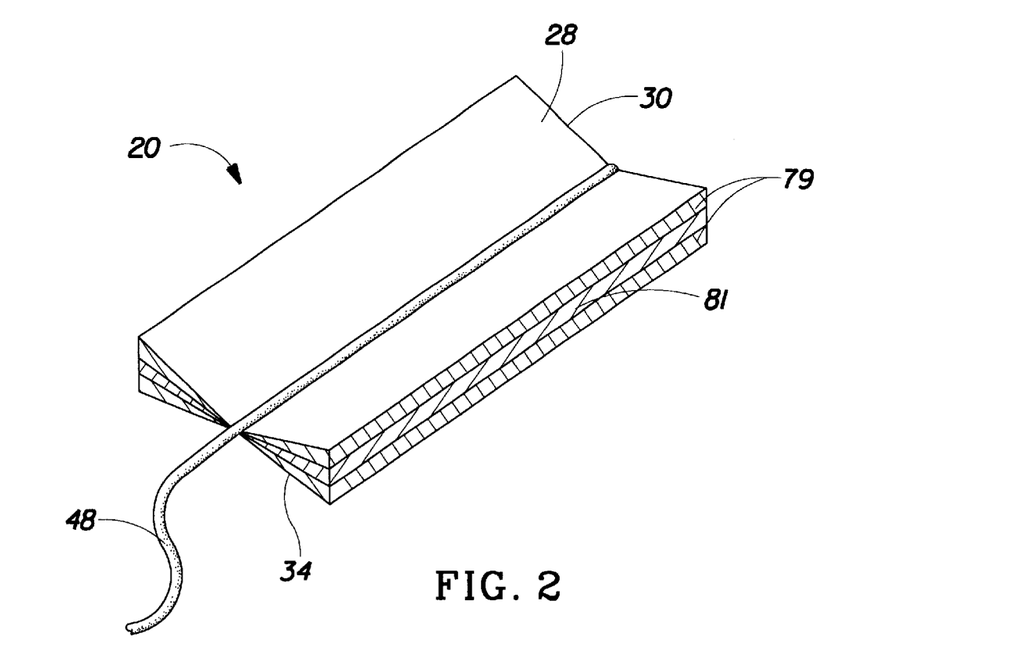
FIG. 2 is a perspective view a typical tampon pledget prior to compression into the primary absorbent member of a tampon of the present invention.
Figure 3:
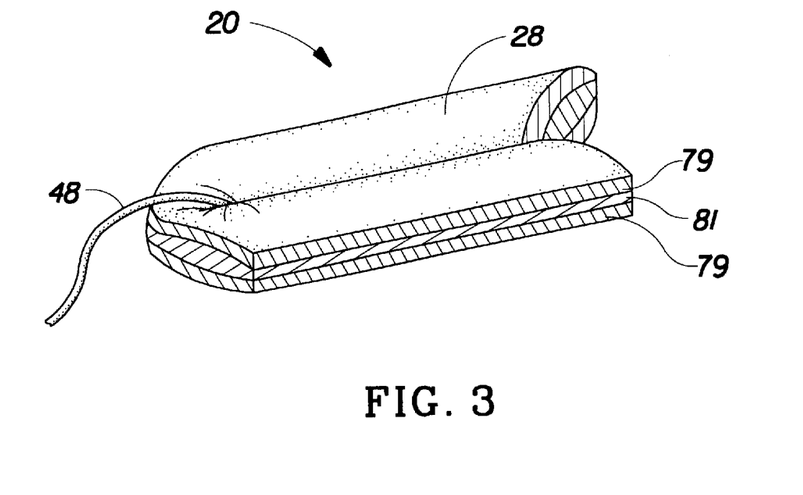
FIG. 3 is a perspective view of another tampon pledget prior to compression into the primary absorbent member of a tampon of the present invention in which the pledget is chevron shaped structure.

The primary absorbent member 21 of the tampon 20 of the present invention may be formed from any suitable tampon pledget, such as tampon pledget 28 shown in FIG. 2. Typically, the secondary absorbent material 60, described in greater detail below, is joined to either a withdrawal mechanism, such as withdrawal cord 48, the primary absorbent member 21 itself, or both. This joining of the secondary absorbent material may occur subsequently to compression of the pledget 28 to form the primary absorbent member 21. In some variations it may be desirable to attach some or all of the secondary absorbent material 60 to the pledget 28, the withdrawal mechanism, such as withdrawal cord 48, or both, prior to compression of the pledget 28 to a self-sustaining form (i.e. the absorbent member 21). In one preferred method of making a tampon 20 of the present invention, described more fully below, the mass of secondary absorbent material 60 is integral with the primary absorbent member 21 prior to compression of the pledget. In any of the above mentioned manners of construction, the secondary absorbent material 60 is preferably not compressed; or, if compressed, is not compressed to the same degree as the primary absorbent member 21.

The tampon pledget 28 portion of the tampon 20 which will be compressed to form the primary absorbent member 21 may be any suitable shape, size, material, or construction. In the embodiment shown in FIG. 2, pledget 28 is a batt of absorbent material which is a generally rectangular pad of absorbent material.

While the pledget 28 shown in FIG. 2 is generally rectangular, other shapes such as trapezoidal, triangular, hemispherical, and chevron shaped are also acceptable. The pledget 28 may be a laminar structure comprised of integral or discrete layers. In the embodiment shown in FIG. 2, the pledget 28 may comprise outer layers 79 and at least one intermediate layer 81 positioned between the outer layers 79. In other embodiments, the pad need not have a layered structure at all. The pledget 28 may comprise a folded structure, may be rolled, may comprise a "petal" structure or any other of the structures which are known in the art with respect to tampon pledgets.

The pledget 28, and consequently, the resulting primary absorbent member 21 of the tampon 20 may be constructed from a wide variety of liquid-absorbing materials commonly used in absorbent articles such as rayon, cotton, or comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; foam; tissue including tissue wraps and tissue laminates; or any equivalent material or combinations of materials, or mixtures of these. Preferred absorbent materials comprise cotton, rayon (including tri-lobal and conventional rayon fibers, and needle punched rayon), folded tissues, woven materials, nonwoven webs, synthetic and/or natural fibers. The tampon 20 and any component thereof may comprise a single material or a combination of materials. Additionally, superabsorbent materials, such as superabsorbent polymers or absorbent gelling materials may be incorporated into the tampon 20.

In the preferred embodiment shown in FIGS. 1 and 2, the pledget 28 and resulting primary absorbent member 21 is formed of a soft absorbent material such as rayon, cotton (including either long fiber cotton or cotton linters) or other suitable natural or synthetic fibers or sheeting. The materials for the tampon 20 can be formed into a fabric, web, or batt that is suitable for use in the pledget 28 by any suitable process such as airlaying, carding, wetlaying, hydroentangling, or other known techniques.

In one non-limiting preferred embodiment, the tampon pledget 28 and resulting primary absorbent member 21 comprise rayon, cotton, or combinations of both materials. The rayon used in the tampon pledget 28 may be any suitable type typically used in disposable absorbent articles intended for in vivo use. Such acceptable types of rayon include GALAXY Rayon (a tri-lobed rayon structure) available as 6140 Rayon from Courtaulds Fibers Ltd., of Hollywall, England. SARILLE L rayon (a round fiber rayon), also available from Courtaulds Fibers Ltd. is also suitable. Any suitable cotton material may be used in the tampon pledget 28. Suitable cotton material includes, long fiber cotton, short fiber cotton, cotton linters, T-fiber cotton, card strips, and comber cotton. Preferably, the cotton layers should be a scoured & bleached cotton absorbent with a glycerin finish, a leomin finish, or other suitable finish.

The absorbent material of the pledget 28 may be surrounded with a liquid permeable overwrap material, if desired. Such overwrap materials may comprise rayon, cotton, bicomponent fibers, or other suitable natural or synthetic fibers known in the art. If the pledget 28 of the present invention is layered, the layers may comprise different materials. For example, in the embodiment shown in FIG.. 2 the outer layers 79, may comprise primarily rayon, while the intermediate layer 81 or layers may comprise primarily cotton. Optionally, the entire pledget 28 may comprise a uniform or non-uniform blend of materials throughout.

The pledget 28 may be any suitable size and thickness suitable for compression into a tampon having a size which facilitates insertion. A size similar to those of conventional currently available tampons has been found to work well. A typical size for such pledgets may be about 9 cm in length and about 4.5 cm in width. One preferred range for the overall basis weight is from about 150 g/m$^2$ to about 750 g/m$^2$. Optionally, pledgets 28 which are shorter and wider than the ranges given above may also be desirable in order to facilitate width-wise expansion of the tampon in use.

A withdrawal mechanism, such as withdrawal cord 48, examples of which are shown in FIGS. 1–2, is preferably joined to the tampon 20 for removal of the tampon after use. The withdrawal mechanism is, preferably joined to at least the primary absorbent member 21 and extends beyond at least the withdrawal end 34 thereof. Any of the withdrawal cords currently known in the art may be used as a suitable withdrawal mechanism. In addition, the withdrawal mechanism can take on other forms such as a ribbon, loop, tab, or the like. The withdrawal mechanism may be integral with, or an extension of another element of the tampon, such as an overwrap as described above. Additionally, as discussed in greater detail below, the withdrawal mechanism may be integral with the mass of secondary absorbent material.

The withdrawal cord 48 or other withdrawal mechanism may be attached in any suitable manner known in the art including sewing, adhesive attachment, or a combination of known bonding methods. The tampon 20 of the present invention may also be provided with more than one withdrawal mechanism such as multiple withdrawal cords 48. For example, two withdrawal cords 48 or other withdrawal mechanisms such withdrawal ribbons may be attached down the length of the pledget 28 and extend from the withdrawal end thereof. In such an instance, the mass of secondary absorbent material, may be joined to one or both of the withdrawal cords 48 or other withdrawal mechanisms.

Especially when the mass of secondary absorbent material 60 is joined to the withdrawal cord 48 or other withdrawal mechanism, the withdrawal cord 48 is preferably non-absorbent along at least the location of such attachment. As used herein, the term "non-absorbent" refers to a structure that does not retain a significant portion of deposited fluid in its structure. The entire withdrawal cord 48 or other withdrawal mechanism may be made non-absorbent, if desired. The materials comprising the withdrawal cord may be inherently non-wettable or hydrophobic, or they may be treated to provide such properties. For example, a coating of wax may be applied to the withdrawal cord 48 to decrease or eliminate its absorbency. Other means for providing a material suitable for use as a withdrawal cord 48 which is non-absorbent and/or non-wicking are known in the art. For example, U.S. Pat. No. 5,458,589 issued to Comin-DuMong describes one such approach. The withdrawal cord 48 or other withdrawal mechanism need not necessarily be non-wicking, even if a non-absorbent withdrawal cord is desired. For example, it may be desirable to provide a withdrawal cord 48 in which at least a portion of the cord has a tendency to wick deposited fluid upwardly toward the withdrawal end 34 of the primary absorbent member and into the structure thereof.

The withdrawal cord 48, withdrawal ribbon, or other withdrawal mechanism need not have uniform properties throughout its length. For example, the portion of the withdrawal cord nearest the primary absorbent member 21 may be absorbent while the lower portion (i.e. furthest from the primary absorbent member 21) of the cord 48 or other withdrawal mechanism may be non-absorbent. Other properties such as wicking ability, hydrophilicity, density, capillary size, width, thickness, and the like may also vary along the length of the withdrawal cord 48 or other withdrawal mechanism. In preferred embodiments, the withdrawal mechanism is preferably flexible.

The withdrawal cord 48 or other withdrawal mechanism may be joined to any suitable location on the tampon 20. In the embodiment shown in FIGS. 1–2, the withdrawal cord 48 is joined to the primary absorbent member 21 (and pledget 28) and extends freely beyond the withdrawal end 34 of the primary absorbent member 21. The withdrawal cord 48, is typically attached to the tampon pledget 28 while the pledget 28 is still uncompressed as shown in FIG. 2. The withdrawal cord 40 may be attached along the entire length one major surface of the pledget 28 (such as by stitching) and hang free from one end, such as the withdrawal end 34.

The tampon 20 of the present invention is also provided with a mass of secondary absorbent material 60. The secondary absorbent material 60 may comprise one piece of material as shown, for example, in FIG. 1, or may comprise multiple discrete pieces as shown, for example in FIG. 5. The secondary absorbent material 60 may be arranged in a wide variety of shapes and configurations and may be generally cylindrical, spherical, semi-spherical, disc-like, planar, rectangular, "skirt-like" in shape, or may comprise "tufts" or whips of absorbent elements.

The size of the secondary absorbent material 60 may vary according to its shape. For example, in the embodiment shown in FIG. 1 the mass of secondary absorbent material 60 is generally cylindrical and elongated. The length of the mass of secondary absorbent material is measured in the direction generally parallel to a line running through the axis of the tampon extending through the insertion end and withdrawal end of the primary absorbent member 21. In the embodiment shown in FIG. 1, the length of the mass of secondary absorbent material 60 may be between about 10 mm and about 55 mm, more preferably 25 mm and about 35 mm.

Caliper measurements given herein are measured using an AMES gage with a 0.25 psig load and a 0.96 inch diameter foot. Those skilled in the art will recognize that if a 0.96 inch diameter foot is not appropriate for a particular sample size, the foot size may be varied while the load on the gauge is accordingly varied to maintain a confining pressure of 0.25 psig. The caliper measurement refers to the diameter of the mass of secondary absorbent material 60 or to its widest dimension in the non-length direction. If the mass of secondary absorbent material 60 is not exactly or substantially cylindrical, "diameter" may be interpreted to mean the widest caliper measurement as defined herein in the non-length direction. The diameter, or caliper, of the mass of secondary absorbent material 60 shown in FIG. 1 is preferably from about 2 mm to about 30 mm, more preferably from about 7 to about 15 mm.

Any suitable amount of fiber may be used for the mass of secondary absorbent material 60. In the preferred embodiment shown in FIG. 1, about 0.05 g of absorbent fiber is used. Preferably, the mass of secondary absorbent material 60 is constructed such that it will remain flexible, in order to facilitate comfort in use.

The mass of secondary absorbent material 60 is joined to the tampon 20 at any suitable location generally proximate the withdrawal end 34 of the primary absorbent member 21. In the embodiment shown in FIG. 1, the mass of secondary absorbent material 60 is joined to the withdrawal cord 48 and is generally centered axially around the cord 48. It is also possible to attach such a mass of secondary absorbent material 60 to the withdrawal end 34 of the primary absorbent member 21 either in addition to, or in lieu of, attachment to the withdrawal cord 48.

Figure 4:
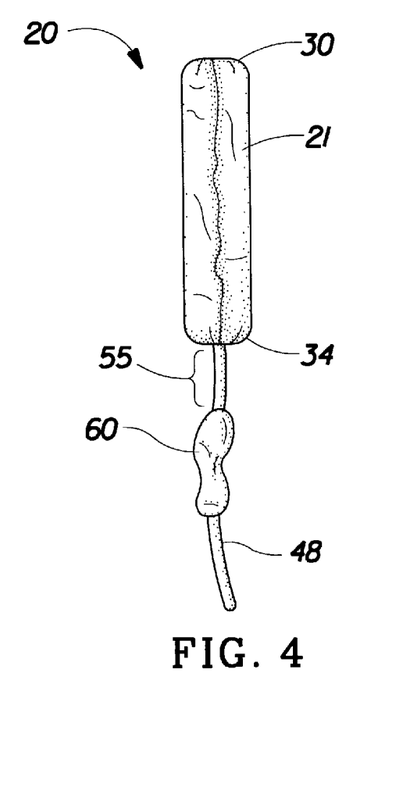
FIG. 4 is front view of an additional embodiment of a tampon of the present invention in which there is a gap between the withdrawal end of primary absorbent member and the mass of secondary absorbent material.
Figure 5:
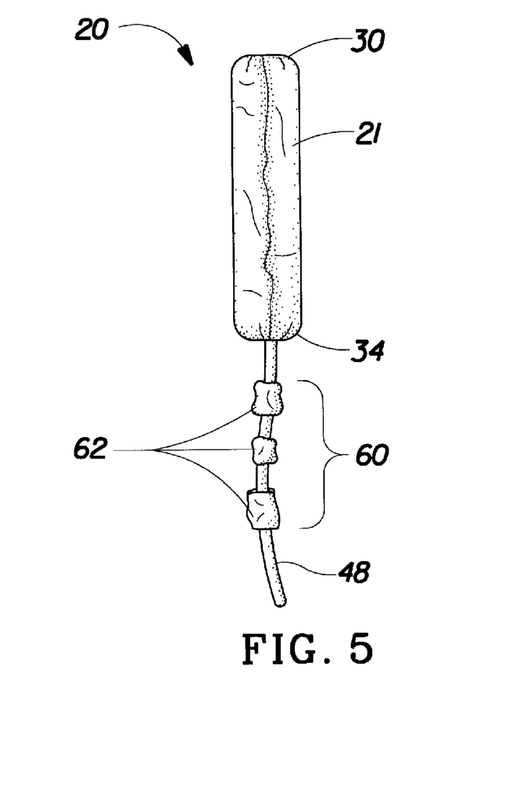
FIG. 5 is a front view of an embodiment of a tampon of the present invention in which the mass of secondary absorbent material is provided in the form of a plurality of discrete pieces of absorbent material.

In the embodiment shown in FIG. 4, the mass of secondary absorbent material 60 is joined to the withdrawal cord 48. The mass of secondary absorbent material 60 in FIG. 4, however, is positioned at a location slightly lower along the withdrawal cord 48 than is the case with FIG. 1, thereby creating a "gap" 55 between the withdrawal end 34 of the primary absorbent member and the uppermost part of the mass of secondary absorbent material 60. The length of the gap 55 along the withdrawal cord 48 may preferably be in the range of from about 1 mm to about 15 mm. As shown in FIG. 5, the mass of secondary absorbent material 60 may comprise a series of discrete pieces of absorbent material 62. In the embodiment shown in FIG. 5, these discrete pieces of absorbent material 62 are attached along the withdrawal cord 48 of the tampon 20.

Figure 6:
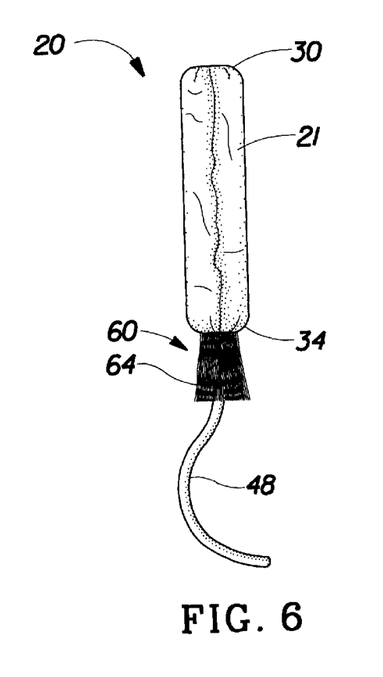
FIG. 6 is a front view of an embodiment of a tampon of the present invention in which the mass of secondary absorbent material is attached to the primary absorbent member.

In the embodiment shown in FIG. 6, the mass of secondary absorbent material 60 is joined to the withdrawal end 34 of the primary absorbent member. The mass of secondary absorbent material 60 shown in FIG. 6 is in the form of a series of absorbent strands or "tufts" 64 of material depending from the withdrawal end 34 of the primary absorbent member 21. These absorbent strands or tufts 64 can also be substantially continuous or be constructed from one piece of material arranged in the form of a "skirt" around the withdrawal end 34 of the primary absorbent member 34.

Figure 7:
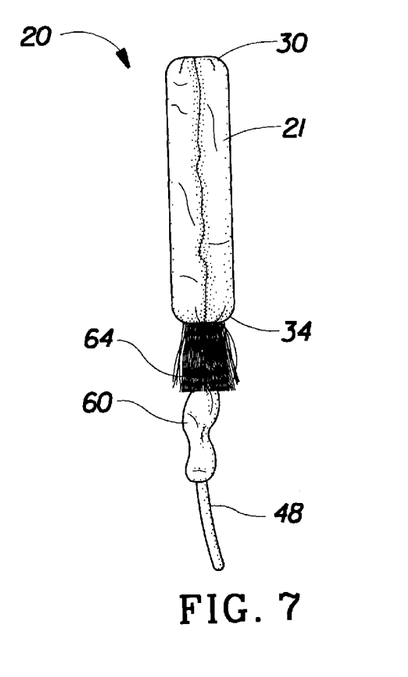
FIG. 7 is a front view of an embodiment of a tampon of the present invention in which a portion of the mass of secondary absorbent material is attached to the primary absorbent member and a portion of the mass of secondary absorbent material is attached to the withdrawal cord.

As shown in FIG. 7, it is possible to combine different variations on the form of the secondary absorbent material 60 described above in the same tampon 20. For example, FIG. 7 shows the combination of a single piece of secondary absorbent material 60 joined to the withdrawal cord 48 used in combination with additional secondary absorbent material 60 in the form of absorbent strands or tufts 64.

In any of the embodiments described above, or in variations thereof, the location of the secondary absorbent material should preferably be generally proximate the withdrawal end of the main absorbent portion 21 of the tampon 20. In preferred embodiments, the length of the primary absorbent member 21 is in the range from about 2 cm to about 7 cm. The withdrawal cord 48 of the tampon 20 preferably extends below the withdrawal end 34 of the primary absorbent portion about 10 cm.

Both the primary absorbent member 21 and the mass of secondary absorbent material 60 preferably reside entirely within the vaginal cavity of the wearer during use of the tampon 20. This is achieved by the relatively closeness of the mass of secondary absorbent material 60 to the withdrawal end 34 of the primary absorbent member 21 as well of the relative size of such mass 60 compared to the overall size of the tampon. In particularly preferred embodiments, only the withdrawal cord 48 or other withdrawal mechanism (without any associated secondary absorbent material 60) resides externally to the orifice of the vagina.

The mass of secondary absorbent material 60 proximate to the withdrawal end of the primary absorbent member 21 adds an effective area of the tampon 20 which is placed "lower" within the vaginal vault (as compared to the effective area of current tampons). Because the secondary absorbent material 60 is preferably located proximate the withdrawal end 34 as described, optimal placement of the effective area of the tampon 20 is achieved by the present invention. The tampon 20 may be inserted in the same manner as most currently available conventional tampons, and the secondary absorbent material (which is preferably fixed and not slidable) will provide absorbent capacity within the lower vaginal vault. Additionally, the preferred configurations and properties of the mass of secondary absorbent material 60 described herein allows for an "operable" portion of the tampon 20 be provided in the lower vaginal vault without introduction of wearer comfort concerns. The lower region of the vaginal vault is highly sensitive and prior art devices located in this region had a tendency to cause discomfort or unacceptable wearing awareness as opposed to devices more fully inserted within the vaginal canal. This concern is not presented by the tampon 20 of the present invention because the portion of the tampon designed to reside in the lowest portion of the vaginal cavity (i.e. the mass of secondary absorbent material 60) is preferably softer, smaller, and less dense than the primary absorbent member.

The term "joined" or "attached" as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element; i.e., one element is essentially part of the other element.

The mass of secondary absorbent material 60 may be joined to the withdrawal cord 48 (or other withdrawal mechanism) or the withdrawal end 34 of the primary absorbent member 21, or both, by any variety of means. For example, the mass of secondary absorbent material 60 may be joined to one or both of the withdrawal cord 48 or the withdrawal end 34 of the primary absorbent member 21 using any suitable adhesive. Such adhesive may extend continuously along the length of attachment or it may be applied in a "dotted" fashion at discrete intervals. Alternatively, the mass of absorbent material 60 may be joined to the withdrawal cord 48 or primary absorbent member 21 by stitching. Such stitching may use cotton or rayon thread. Other attachment mechanisms include thermally bonding (for example where the mass of secondary absorbent material 60 has thermally bonded fibers or other thermally bonding materials incorporated therein), fusion bonding, or any other suitable means known in the art for joining such materials.

The mass of secondary absorbent material 60 may be constructed from any of the materials described above for suitable as use in the primary absorbent member 21. Preferably, the same materials are used in the construction of the mass of secondary absorbent material 60 as are used in the primary absorbent member 21. Rayon and cotton are especially preferred materials for inclusion in the mass of secondary absorbent material 60. The mass of secondary absorbent material 60 may also include a suitable nonwoven structure as described above. A layer or sheet of secondary absorbent material 60 may be formed independently of the primary absorbent member 21 and slipped around the withdrawal cord 48 and attached thereto. The withdrawal cord 48 could be wound with an absorbent material, fiber, yarn, or other structure, in at least the portion of the cord 48 located proximate to the withdrawal end 34 of the primary absorbent member 21.

The mass of secondary absorbent material 60 may also be integral with any other component of the tampon 20. For example, the mass of secondary absorbent material 60 may comprise an extension of the primary absorbent member (although preferably a less compressed portion). The mass of secondary absorbent material 60 may be in the form of a sheet or layer of absorbent material. For example, one or more internal layers 81 such as that shown in FIG. 2 could extend beyond the withdrawal end 34 of the pledget 28 either along its entire width or a portion of its width to form the mass of secondary absorbent material. A portion of the overwrap, if included, could be extended as described herein to form the mass of secondary absorbent material. Additionally, the withdrawal mechanism itself could serve as both such a withdrawal mechanism and the secondary absorbent material. An example of such an embodiment is a ribbon of material which serves as the withdrawal mechanism. The upper portion of this ribbon could be absorbent and serve as the mass of secondary absorbent material while the lower portion of such ribbon is non-absorbent.

The mass of secondary absorbent material 60 is preferably absorbent. While the specific absorbency of the secondary absorbency material 60 may be less than, equal to, or greater than that of the primary absorbent member 21; preferably, the total absorbency of the mass of secondary absorbent material 60 is less than that of the primary absorbent member 21. In embodiments such as that shown in FIG. 5 where the mass of secondary absorbent material 60 is comprised of multiple pieces of absorbent material, the primary absorbent member 21 preferably has a total absorbency which exceeds the total combined absorbency of such multiple pieces of secondary absorbent material 60.

The mass of secondary absorbent material 60 is preferably hydrophilic. In preferred embodiments, the mass of secondary absorbent material 60 may have an advancing contact angle greater than the advancing contact angle of the primary absorbent member 21 and/or the withdrawal cord 48 (or other withdrawal mechanism), such that fluid is preferentially directed toward and absorbed by the primary absorbent member 21. Optionally, the mass of secondary absorbent material 60 may be treated to make it less absorbent than the primary absorbent member 21. Preferably, the majority of the fluid absorbed and retained by the tampon 20 will ultimately be retained in the primary absorbent member 21. In preferred embodiments, the mass of secondary absorbent material 60 is more hydrophilic than the withdrawal cord 48 or other withdrawal mechanism. The withdrawal cord 48, may be made substantially hydrophobic in preferred executions. If the entire withdrawal cord 48 or other withdrawal mechanism is not less hydrophilic than the mass of secondary absorbent material 60, preferably, at least potions of the withdrawal mechanism (such as along the location of attachment of the mass of secondary absorbent material to the withdrawal cord) are less hydrophilic than the mass of secondary absorbent material.

For a more detailed description of hydrophilicity and contact angles see the following publications which are incorporated by reference herein: The American Chemical Society Publication entitled "Contact Angle, Wettability, and Adhesion," edited by Robert F. Gould, and copyrighted in 1964; and TRI/Princeton Publications, Publication Number 459, entitled "A Microtechnique for Determining Surface Tension," published in April 1992, and Publication Number 468 entitled, "Determining Contact Angles Within Porous Networks," published in January, 1993, both edited by Dr. H. G. Heilweil.

The mass of secondary absorbent material 60 may optionally be provided with a mechanism to preferentially direct acquired fluid toward the body of the primary absorbent member 21. Examples of such a driving force are the use of a hydrophilicity gradient as described above. Other mechanisms include a density or capilarity gradient, or an osmotic driving force. The mass of secondary absorbent material 60 may be provided with loose fiber ends to add a textured surface to the material 60. Capillary channel fibers may optionally be incorporated into the mass of secondary absorbent material 60 in order to provide the driving force for acquired fluid described herein.

Preferably, the density of material which comprises the mass of secondary absorbent material 60 is lower than the density of the primary absorbent member 21. The mass of secondary absorbent material 60 is preferably not compressed during formation of the tampon 20. If the mass of secondary absorbent material 60 is compressed it is preferably compressed to a lesser degree than the primary absorbent portion such that the resulting density of the secondary absorbent material 60 in the finished tampon 20 remains below that associated with the primary absorbent member 21.

The tampon 20 of the present invention is believed to offer several advantages over prior art tampons. As noted previously, the incorporation of the mass of secondary absorbent material 60 provides absorbency capacity in the lower vaginal vault. This results in a lower disposition of the overall "effective" surfaces of the tampon 20 within the vaginal vault of the wearer. Additionally, because the mass of secondary absorbent material is less compressed than the primary absorbent member 21, such material is available to immediately acquire fluid without the need for re-expansion. Previously known device, such as that described in U.S. Pat. No. 3,101,714 (Penska) required a two step insertion process. That is, the Penska device must be inserted, then the slidable plug must be moved into place. This plug would not be fully inserted past the vaginal sphincter muscles and would have high wearing awareness due to contact with and subsequent stretching of the introitus. The present invention, by contrast, is inserted in one operation, and by its design is properly positioned for optimal effectiveness following this one-step insertion process. The tampon of the present invention also has the advantage that its provides the additional benefits over current tampons described herein, but does not require a change in consumer use habits to use properly and effectively. The tampon of the present invention additionally may be constructed with currently known safe and effective materials and provides an increase in leakage protection without requiring an increase in the overall absorbency of the tampon (as measured, e.g. by the syngyna method).

To form a tampon ready for use, the tampon pledget 28 is typically compressed and heat conditioned in any suitable conventional manner. Pressures and temperatures suitable for this purpose are well known in the art. Typically, the pledget 28 is compressed in both the radial and axial direction using any means well known in the art. While a variety of techniques are known and acceptable for these purposes, a modified tampon compressor machine available from Hauni Machines, Richmond, Va., is suitable. If the mass of secondary absorbent material 60 is attached to the tampon 20 after compression of the pledget 28, then no modification of the method of making a conventional compressed absorbent tampon is necessary (except of course that the mass of secondary material is attached after the otherwise completed tampon is formed).

While several methods of making a tampon 20 of the present invention would be apparent to one of skill in the art in light of the disclosure herein, following is a description of one method of making a tampon of the present invention is a continuous operation in which the mass of secondary absorbent material is integral with the tampon pledget 28.

Figure 8:
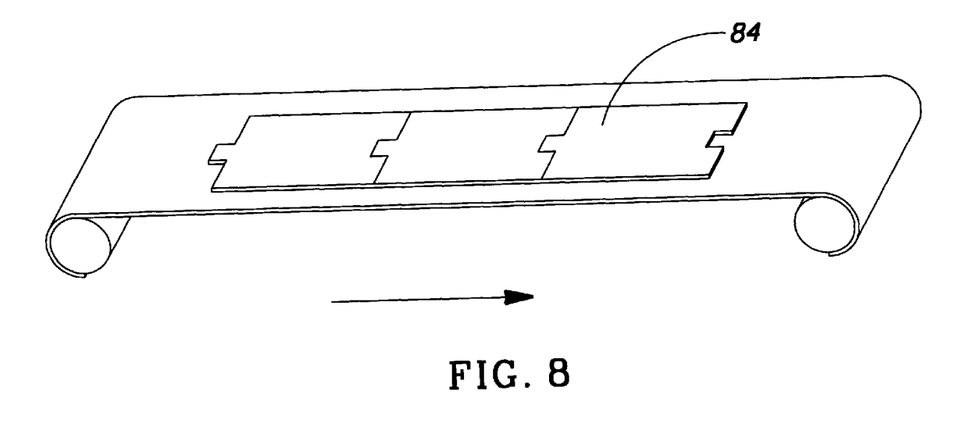
FIG. 8 shows one method of making one or more tampons of the present invention in which multiple pads may be cut from a continuous strip of absorbent material.
Figure 9:
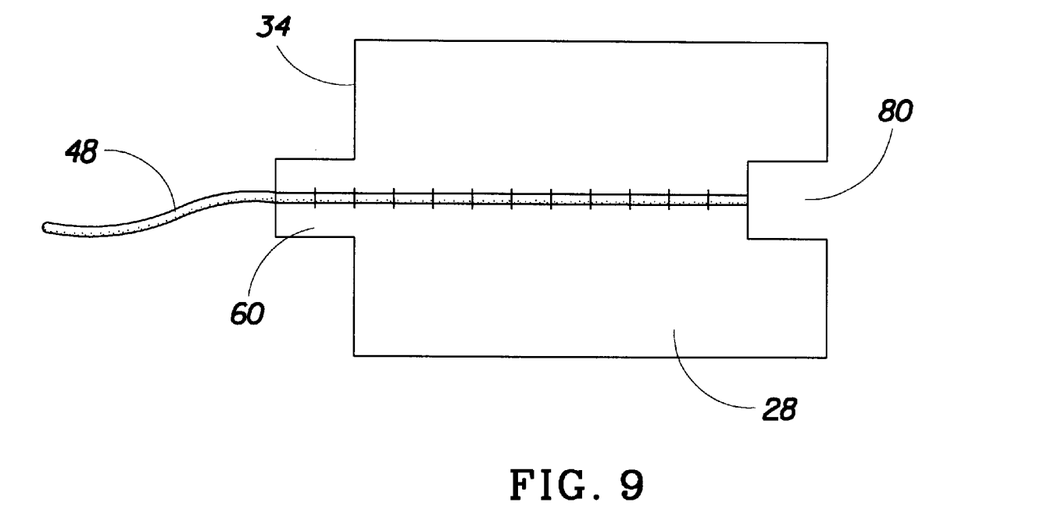
FIG. 9 shows a pad which has been cut from the continuous strip of absorbent material of FIG. 8 and to which a withdrawal cord has been attached prior to compression.

In such a method of making, a generally rectangular (or other suitably shaped) pad of absorbent material is formed. FIG. 8 shows a strip of absorbent material formed by a suitable carding process. The carding process results in a continuous strip of absorbent material 84 which may then be cut into individual absorbent pads, such as those shown in FIG. 9. The term "continuous strip" is intended to mean an elongated mass of absorbent material of sufficient length in the machine direction to be cut into two or more individual pledgets 28. The cutting operation may be performed (i.e. through the use of a suitably shaped cutting die) such that a "notch" 80 is formed in the insertion end of each pledget 28. This notch 80 will result in an integral piece of absorbent material which depends from the withdrawal end 34 of the pledget 28. The notch 80 may be generally square or rectangular as shown in FIG. 9 or may be triangular, semi-circular, trapezoidal, or any of the other shapes disclosed herein for the mass of secondary absorbent material 60. This notch 80, as shown in FIG. 9 will serve as the mass of secondary absorbent material 60 of the finished tampon. The individual pads are then preferably provided with a suitable withdrawal cord 48 which may extend down the entire length of the pledget 28 and mass of secondary absorbent material 60.

During formation of the tampon 20 the pledget 28 (exclusive of the integral mass of secondary absorbent material) is compressed as described above. Because the mass of secondary absorbent material is smaller in the width dimension than the pledget 28, the radial compression of the pledget 28 will not substantially compress the secondary absorbent material 60. During the axial compression stage, if any, only the pledget 28 portion is compressed through the use of a suitable push-rod and the mass of secondary absorbent material remains essentially non-compressed.

The tampon 20 of the present invention may be inserted digitally or through the use of an applicator. If the tampon 20 is to be used for digital insertion, it may be desirable to form the pledget from a layer of absorbent material which has been rolled into a cylindrical shape.

Any of the currently available tampon applicators may also be used for insertion of the tampon of the present invention. Such applicators of typically a "tube and plunger" type arrangement and may be plastic, paper, or other suitable material. Additionally, a "compact" type applicator is also suitable. The applicator plunger will push the compressed primary absorbent member 21 out of the applicator while fitting around the mass of secondary absorbent material 60.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

The disclosures of all patents and patent applications referred to in this specification (including those listed in the Cross Reference to Related Applications Section) are hereby incorporated by reference as if fully set forth herein. While particular embodiments of the present invention have been illustrated and described, it would be obvious to those skilled in the art that various other changes and modifications can be made without departing from the spirit and scope of the invention.

What is claimed is:

1. A catamenial tampon for use within the vaginal space of a female wearer, said tampon comprising:

a primary absorbent member constructed from an absorbent material compressed to a substantially cylindrical self-sustaining form, said primary absorbent member having an insertion end and a withdrawal end;

a mass of secondary absorbent material proximate said withdrawal end of said primary absorbent member, said mass of secondary absorbent material having a density which is lower than the density of said primary absorbent member; and wherein said primary absorbent member has a first diameter and said mass of secondary absorbent material has a second diameter, and wherein said first diameter is larger than said second diameter.

2. The tampon of claim 1 further comprising a withdrawal mechanism attached to said primary absorbent member and extending beyond at least said withdrawal end, wherein said mass of secondary absorbent material is substantially axially centered about said withdrawal mechanism.

3. The tampon of claim 1 further comprising a withdrawal mechanism attached to said primary absorbent member and extending beyond at least said withdrawal end, wherein said mass of secondary absorbent material is joined to said withdrawal mechanism.

4. The tampon of claim 1 by wherein said mass of secondary absorbent material is joined to said withdrawal end of said primary absorbent member.

5. The tampon of claim 1 wherein said tampon comprises a gap between said withdrawal end of said primary absorbent member and said mass of secondary absorbent material.

6. The tampon of claim 1 wherein said mass of secondary absorbent material comprises a plurality of discrete pieces of absorbent material.

7. The tampon of claim 1 wherein at least a portion of said mass of secondary absorbent material is provided with a driving mechanism to direct absorbed fluid toward said primary absorbent member of said tampon.

8. The tampon of claim 1 wherein said mass of secondary absorbent material comprises a nonwoven web attached to said withdrawal end of said primary absorbent member.

9. The tampon of claim 1 wherein said primary absorbent member and said mass of secondary absorbent material are configured such that said primary absorbent member and mass of said secondary absorbent material reside entirely within said vaginal space during use without extending outwardly therefrom.

* * * * *